US010537622B2

(12) United States Patent
Bioley et al.

(10) Patent No.: US 10,537,622 B2
(45) Date of Patent: Jan. 21, 2020

(54) GAS-FILLED MICROVESICLES FOR USE AS VACCINE

(71) Applicant: BRACCO SUISSE SA, Manno (CH)

(72) Inventors: Gilles Bioley, Fiez (CH); Philippe Bussat, Pers-Jussy (FR); Blaise Corthesy, Thierrens (CH); Anne Lassus, Carouge (CH)

(73) Assignee: BRACCO SUISSE S.A., Manno (CH)

( * ) Notice: Subject to any disclaimer, the term of this patent is extended or adjusted under 35 U.S.C. 154(b) by 0 days.

(21) Appl. No.: 15/536,458

(22) PCT Filed: Dec. 21, 2015

(86) PCT No.: PCT/EP2015/080879
§ 371 (c)(1),
(2) Date: Jun. 15, 2017

(87) PCT Pub. No.: WO2016/102515
PCT Pub. Date: Jun. 30, 2016

(65) Prior Publication Data
US 2017/0348401 A1    Dec. 7, 2017

(30) Foreign Application Priority Data

Dec. 22, 2014 (EP) .................................. 14199705

(51) Int. Cl.
  *A61K 39/00*   (2006.01)
  *A61K 39/39*   (2006.01)
  *A61K 47/69*   (2017.01)
  *A61K 49/22*   (2006.01)
(52) U.S. Cl.
  CPC .......... *A61K 39/0005* (2013.01); *A61K 39/39* (2013.01); *A61K 47/6925* (2017.08); *A61K 49/223* (2013.01); *A61K 2039/55555* (2013.01); *A61K 2039/577* (2013.01); *A61K 2039/60* (2013.01); *A61K 2039/6018* (2013.01)
(58) Field of Classification Search
  CPC .. A61K 2039/6018; A61K 2039/55555; A61K 2039/577; A61K 2039/60; A61K 39/39; A61K 39/0005; A61K 49/223; A61K 47/6925
  See application file for complete search history.

(56) References Cited

U.S. PATENT DOCUMENTS

| 5,271,928 A | 12/1993 | Schneider et al. |
| 5,413,774 A | 5/1995 | Schneider et al. |
| 5,445,813 A | 8/1995 | Schneider et al. |
| 5,556,610 A | 9/1996 | Yan et al. |
| 5,597,549 A | 1/1997 | Schneider et al. |
| 5,605,673 A | 2/1997 | Schutt et al. |
| 5,827,504 A | 10/1998 | Yan et al. |

FOREIGN PATENT DOCUMENTS

| CN | 100546649 C | 10/2009 |
| EP | 0554213 A1 | 8/1993 |
| WO | 1991-015244 A2 | 10/1991 |
| WO | 1994-009829 A1 | 5/1994 |
| WO | 1997-029782 A1 | 8/1997 |
| WO | 2004-069284 A2 | 8/2004 |
| WO | 2012-085072 A1 | 6/2012 |
| WO | 2014-096165 A2 | 6/2014 |

OTHER PUBLICATIONS

Reed, Steven G. et al., "New horizons in adjuvants for vaccine development", Trends in Immunology, 2008, 30(1): 23-32, Elsevier Ltd.
Tanaka, Yuriko et al., "Liposomes with Differential Lipid Components Exert Differential Adjuvanticity in Antigen-Liposome Conjugates via Differential Recognition by Macrophages", Bioconjugate Chemistry, 2004, vol. 15, No. 1, pp. 35-40, doi:10.102/bc034134, American Chemical Society.
Wilson-Welder, Jennifer H. et al., "Vaccine Adjuvants: Current Challenges and Future Approaches", Journal of Pharmaceutical Sciences, 2009; vol. 98, No. 4, pp. 1278-1316, Wiley InterScience, doi:10.1002/jps.21523.
European Search Report for European application No. 14199705.6, dated Jul. 23, 2015.
International Search Report and Written Opinion for PCT application No. PCT/EP2015/080879, dated Feb. 3, 2016.
Office Action for European application No. EP158201392, dated Sep. 26, 2018.

*Primary Examiner* — Michael G. Hartley
*Assistant Examiner* — Leah H Schlientz
(74) *Attorney, Agent, or Firm* — Vivicar Law, PLLC

(57) ABSTRACT

Gas-filled microvesicles comprising an antigen bound thereto and to aqueous suspensions containing said microvesicles, for use in immunomodulating formulations, in particular as a vaccine. The antigen is covalently bound to a component of the microvesicles envelope. The microvesicles of the invention, comprising a molar excess of fatty acids in the stabilizing envelope, are particularly effective in the uptake by antigen-presenting cells, in particular dendritic cells.

16 Claims, No Drawings

GAS-FILLED MICROVESICLES FOR USE AS VACCINE

CROSS-REFERENCE TO RELATED APPLICATIONS

This application is the national stage application of corresponding International Application Number PCT/EP2015/080879, filed Dec. 21, 2015, which claims priority to and the benefit of European Application Number EP14199705.6, filed Dec. 22, 2014, all of which are hereby incorporated by reference in their entirety.

TECHNICAL FIELD

The invention relates in general terms to gas-filled microvesicles comprising an antigen bound thereto and to aqueous suspensions containing said microvesicles, for use in particular in vaccine and in immunomodulating formulations.

BACKGROUND OF THE INVENTION

Dendritic cells (DC) play a pivotal role in the initiation and modulation of adaptive immunity through the release of polarizing cytokines, as well as the processing and presentation of captured antigen (Ag) to prime or recall specific T cell responses. Immunotherapy strategies, including vaccination, aiming at modulating immune responses, have been focusing on the delivery of Ag to these professional antigen-presenting cells (APC). Vaccination is usually achieved by the in vivo delivery of antigenic entities (DNA, peptides or proteins), that are, due to their low immunological activities, generally formulated in adjuvanted delivery systems.

Several delivery systems have been investigated during the past years, where different adjuvants, based in particular on Ag particulation, have been tested for their efficacy in enhancing antigen delivery and thus activating the immune system. For instance, the adjuvant effect of liposomes in antigen-liposomes formulations has been investigated (see e.g.: Tanaka et al, "Liposomes with Differential Lipid Components Exert Differential Adjuvanticity in Antigen-Liposome Conjugates via Differential Recognition by Macrophages", Bioconjugate Chem., Vol. 15 (1), 2004, pp. 35-40). More recently, also gas-filled microvesicles have been proposed as immune adjuvants and vaccine carriers, as disclosed in Chinese Patent CN 10054664. Gas-filled microvesicles are generally known for their use as contrast agents, particularly for ultrasound imaging. They typically include suspensions of gas bubbles having a diameter of a few microns dispersed in an aqueous medium and comprise suitable materials forming a stabilizing envelope for containing the gas.

CN 10054664 discloses in particular the preparation of gas-filled microvesicles where an antigen is either encapsulated inside the microvesicle or adhered to the surface thereto (by static electrical adsorption). The microvesicles are then administered topically and ultrasonic waves are applied locally, to destroy the microvesicles and release the antigen. According to said patent, contrary to the positive effects observed with combined use of gas-filled microvesicles and ultrasound irradiation, the sole administration of microvesicles with an antigen adhered thereto is substantially ineffective (comparable to a blank control).

International Patent Application WO 2012/085072 discloses gas-filled microvesicles where the antigen is covalently bound to a component of the microvesicle envelope, in particular a phospholipid, these microvesicles providing a remarkable adjuvant effect in the substantial absence of any ultrasound irradiation.

The Applicant has now found that by suitably modifying the formulation of the stabilizing envelope of the gas-filled microvesicles the adjuvant effect of the microvesicle may be further increased. In particular, the Applicant has observed that advantageous results in immunomodulating treatments can be achieved when the molar amount of fatty acids in the stabilizing envelope of the microvesicles is higher than the molar amount of phospholipids; further advantages can be achieved when the antigen is directly linked to a phospholipid.

SUMMARY OF THE INVENTION

An aspect of the invention relates to a pharmaceutical formulation comprising an aqueous suspension of gas-filled microvesicles with a stabilizing envelope, said stabilizing envelope comprising (a) an antigen covalently bound to an amphiphilic component forming said envelope, (b) a phospholipid and (c) a fatty acid, wherein the molar ratio between the phospholipid and the fatty acid is of at least 40/60 or lower.

Preferably said molar ratio is of 30/70 or lower, more preferably of at least 25/75 or lower and even more preferably of 22/78 or lower.

According to a preferred embodiment, the amount of phospholipid in the stabilizing envelope is less than 50% by weight with respect to the total amount of the components forming the envelope.

According to a preferred aspect said formulation is for use in an immunomodulating treatment, preferably in a treatment for promoting antigen-specific antibody response and/or T cell response.

According to a further preferred aspect, said immunomodulating treatment comprises vaccination.

According to a further preferred embodiment, said antigen is a vaccine antigen.

According to another aspect, the invention relates to the use of an aqueous suspension of gas-filled microvesicles comprising an antigen covalently bound to a component of said microvesicles for preparing a vaccine or an immunomodulating agent.

Another aspect of the invention relates to a method for increasing the activation of an antigen-presenting cell by a gas-filled microvesicle comprising a respective antigen and/or increasing the uptake of said antigen by said respective antigen-presenting cell, which comprises contacting said gas-filled microvesicle with said cell, wherein said gas-filled microvesicle comprises a stabilizing envelope comprising (a) said antigen covalently bound to an amphiphilic component forming said envelope, (b) a phospholipid and (c) a fatty acid, wherein the molar ratio between the phospholipid and the fatty acid is of at least 40/60 or lower. According to a preferred embodiment, said antigen-presenting cell is a dendritic cell.

A further aspect of the invention relates to a method for inducing modulation of the immune system in a patient in need thereof which comprises administering to said patient an effective amount of an aqueous suspension of gas-filled microvesicles comprising an antigen covalently bound to a component of said microvesicles.

DETAILED DESCRIPTION OF THE INVENTION

The term "gas-filled microvesicles" includes any structure comprising bubbles of gas of micronic or nanometric size surrounded by an envelope or layer (including film-form layers) of a stabilizing material. The term includes what is known in the art as gas-filled liposomes, microbubbles, microspheres, microballoons or microcapsules. The stabilizing material can be any material typically known in the art including, for instance, surfactants, lipids, sphingolipids, oligolipids, glycolipids, phospholipids, proteins, polypeptides, carbohydrates, and synthetic or natural polymeric materials.

The term "precursor" of a gas-filled microvesicle includes any composition which, upon reconstitution with an aqueous carrier in the presence of a gas, will produce an aqueous suspension of gas-filled microvesicles. Said compositions typically include any of the above-cited stabilizing materials in dry powdered form (e.g. freeze-dried, lyophilized or spray-dried) capable of forming gas-filled microvesicles upon shaking an aqueous suspension thereof in the presence of a gas.

The term "microbubbles" includes aqueous suspensions in which the bubbles of gas are bounded at the gas/liquid interface by a very thin envelope (film) involving a stabilizing amphiphilic material disposed at the gas to liquid interface (sometimes referred to in the art as an "evanescent" envelope); preferably the amphiphilic material comprises mixtures of phospholipids and fatty acids. Microbubble suspensions can be prepared by contacting a suitable precursor thereof, such as powdered amphiphilic materials (e.g. freeze-dried preformed liposomes or freeze-dried or spray-dried phospholipid solutions) with air or other gas and then with an aqueous carrier, while agitating to generate a microbubble suspension which can then be administered, preferably shortly after its preparation. Examples of aqueous suspensions of gas microbubbles, of precursors and of the preparation thereof are disclosed, for instance, in U.S. Pat. Nos. 5,271,928, 5,445,813, 5,413,774, 5,556,610, 5,597, 549, 5,827,504 and WO 04/069284, which are here incorporated by reference.

The expression "envelope-forming compound" includes any compound which is capable of participating to the formation of the stabilizing envelope of gas-filled microvesicles. Said compound is preferably an amphiphilic material, preferably comprising a phospholipid.

The term "immunomodulation" or "modulation of immune response" comprises within its meanings any medical treatment ("immunomodulating treatment") directed to or capable of inducing immunostimulation and/or tolerance in a patient in need thereof. Similarly, the term "immunomodulator" or "immunomodulating" compound or formulation is intended to comprise immunostimulating and/or tolerogenic compounds or formulations, capable of inducing the desired modulation of the immune response in the patient.

The term "immunostimulation" comprises any increase in the immunogenicity of an antigen to induce an improved response in a patient. Similarly "immunostimulating" compounds or formulations comprise compounds or formulations capable of increasing said immune response (useful, for instance, in the treatment of infections, cancers and/or immunodeficiency diseases).

The term "tolerance" comprises within its meanings any state of substantial non-responsiveness of the immune system of a patient to an antigen. "Tolerogens" includes compounds or formulations capable of inducing tolerance to an antigen in a patient (useful for instance, in the treatment of allergies, such as environmental—e.g. pollen—allergies or nutritional allergies).

The term "vaccination" comprises any immunomodulating treatment comprising the administration of an antigen compound or formulation, typically a vaccine antigen, to a patient. Similarly, the term vaccine comprises within its meanings any compound or formulation comprising a vaccine antigen The term "(medical) treatment" comprises within its meaning either prophylactic treatment and/or therapeutic treatment.

Gas-filled microvesicles according to the invention can be any gas-filled microvesicle known in the art, particularly gas-filled microbubbles.

Gas-filled microbubbles are generally stabilized by one or more amphiphilic component. Amphiphilic components suitable for forming a stabilizing envelope of microbubbles comprise, for instance, phospholipids; lysophospholipids; fatty acids, such as palmitic acid, stearic acid, arachidonic acid or oleic acid; lipids bearing polymers, such as chitin, hyaluronic acid, polyvinylpyrrolidone or polyethylene glycol (PEG), also referred as "pegylated lipids"; lipids bearing sulfonated mono- di-, oligo- or polysaccharides; cholesterol, cholesterol sulfate or cholesterol hemisuccinate; tocopherol hemisuccinate; lipids with ether or ester-linked fatty acids; polymerized lipids; diacetyl phosphate; dicetyl phosphate; ceramides; polyoxyethylene fatty acid esters (such as polyoxyethylene fatty acid stearates), polyoxyethylene fatty alcohols, polyoxyethylene fatty alcohol ethers, polyoxyethylated sorbitan fatty acid esters, glycerol polyethylene glycol ricinoleate, ethoxylated soybean sterols, ethoxylated castor oil or ethylene oxide (EO) and propylene oxide (PO) block copolymers; sterol aliphatic acid esters including, cholesterol butyrate, cholesterol iso-butyrate, cholesterol palmitate, cholesterol stearate, lanosterol acetate, ergosterol palmitate, or phytosterol n-butyrate; sterol esters of sugar acids including cholesterol glucuronides, lanosterol glucuronides, 7-dehydrocholesterol glucuronide, ergosterol glucuronide, cholesterol gluconate, lanosterol gluconate, or ergosterol gluconate; esters of sugar acids and alcohols including lauryl glucuronide, stearoyl glucuronide, myristoyl glucuronide, lauryl gluconate, myristoyl gluconate, or stearoyl gluconate; esters of sugars with aliphatic acids including sucrose laurate, fructose laurate, sucrose palmitate, sucrose stearate, glucuronic acid, gluconic acid or polyuronic acid; saponins including sarsasapogenin, smilagenin, hederagenin, oleanolic acid, or digitoxigenin; glycerol or glycerol esters including glycerol tripalmitate, glycerol distearate, glycerol tristearate, glycerol dimyristate, glycerol trimyristate, glycerol dilaurate, glycerol trilaurate, glycerol dipalmitate; long chain alcohols including n-decyl alcohol, lauryl alcohol, myristyl alcohol, cetyl alcohol, or n-octadecyl alcohol; 6-(5-cholesten-3β-yloxy)-1-thio-β-D-galactopyranoside; digalactosyldiglyceride; 6-(5-cholesten-3β-yloxy)hexyl-6-amino-6-deoxy-1-thio-β-D-galactopyranoside; 6-(5-cholesten-3β-yloxy)hexyl-6-amino-6-deoxy)-1-thio-β-D-mannopyranoside; 12-(((7'-diethylaminocoumarin-3-yl)carbonyl)methylamino) octadecanoic acid; N-[12-(((7'-diethylaminocoumarin-3-yl) carbonyl)methylamino)octadecanoyl]-2-aminopalmitic acid; N-succinyldioleylphosphatidylethanolamine; 1,2-dioleyl-sn-glycerol; 1,2-dipalmitoyl-sn-3-succinylglycerol; 1,3-dipalmitoyl-2-succinylglycerol; 1-hexadecyl-2-palmitoyl-glycerophosphoethanolamine or palmitoylhomocysteine; alkylamines or alkylammonium salts, comprising at least one ($C_{10}$-$C_{20}$), preferably ($C_{14}$-$C_{18}$), alkyl chain, such as, for instance, N-stearylamine, N,N'-distearylamine, N-hexadecylamine, N,N'-dihexadecylamine, N-stearylammonium chloride, N,N'-distearylammonium chloride, N-hexadecylammonium chloride, N,N'-dihexadecylammonium chloride, dimethyldioctadecylammonium bromide (DDAB), hexadecyltrimethylammonium bromide (CTAB); tertiary or quaternary ammonium salts comprising one or preferably two ($C_{10}$-$C_{20}$), preferably ($C_{14}$-$C_{18}$), acyl chain linked to the N-atom through a ($C_3$-$C_6$) alkylene bridge, such as, for instance, 1,2-distearoyl-3-trimethylammonium-propane (DSTAP), 1,2-dipalmitoyl-3-trimethylammonium-propane (DPTAP), 1,2-oleoyl-3-trimethylammonium-propane (DOTAP), 1,2-distearoyl-3-dimethylammonium-propane (DSDAP); and mixtures or combinations thereof.

According to the present invention, it has been observed that the efficacy of the microvesicles can be increased when the molar amount of fatty acids in the composition of the stabilizing layer is higher than the molar amount of phospholipids. In particular, it has been observed that high amounts of fatty acids in the envelope of the microvesicle may markedly promote antigen-specific antibody and/or T cell responses in vivo.

Examples of suitable fatty acids are carboxylic acids comprising a relatively long aliphatic chain, e.g. from 10 to 28 carbon atoms ($C_{10}$-$C_{28}$). The aliphatic chain is preferably a linear (straight) chain. The fatty acids useful in a composition according to the invention preferably have a $C_{10}$-$C_{24}$, aliphatic chain, more preferably $C_{14}$-$C_{22}$ and even more preferably, $C_{16}$-$C_{20}$ aliphatic chain terminated by a carboxylic group.

Fatty acids can be either saturated or unsaturated (i.e. containing one or more unsaturations, typically a double bond).

Saturated fatty acids comprise fatty acids with no unsaturations in the aliphatic chain such as, for instance: capric (n-decanoic), lauric (n-dodecanoic), myristic (n-tetradecanoic), palmitic (n-hexadecanoic), stearic (n-octadecanoic), arachidic (n-eicosanoic), behenic (n-docosanoic) and n-tetracosanoic acid. Preferred saturated fatty acids are myristic, palmitic, stearic and arachidic acid, particularly preferred being palmitic acid.

Unsaturated fatty acids may comprise at least one and up to five unsaturations (double bonds in particular) in the aliphatic chain. Preferably the unsaturations are in the cis-configuration. Preferably, the unsaturated fatty acid comprises three or less unsaturations, more preferably two or less unsaturations; particularly preferred are unsaturated fatty acids comprising a single unsaturation in the aliphatic chain. Examples of unsaturated fatty acids comprise, for instance, decenoic, dodecenoic, tetradecenoic, hexadecenoic, hexadecendioc, octadecenoic, octadecadienoic, octadecatrienoic, octadecatetraenoic, eicosenoic, eicosadienoic, eicosatrienoic, eicosatetraenoic, eicospentaenoic, docosenoic, docosatrienoic, docosatetraenoic, docosapentaenoic and tetracosenoic acid. Preferred unsaturated fatty acids comprise myristoleic (cis-9-tetradecenoic), palmitoleic (cis-9-hexadecenoic), sapienic (cis-6-hexadecenoic), oleic (cis-9-octadecenoic), linoleic (cis-9,12-octadecadienoic), linolenic (cis-9,12,15-octadecatrienoic), gondoic (cis-11-eicosenoic), cis-11,14-eicosadienoic, cis-5,8,11-eicosatrienoic, cis-8,11,14-eicosatrienoic, cis-11,14,17-eicosatrienoic, arachidonic (cis-8,11,14,17-eicosatetraenoic) and erucic (cis-13-docosenoic) acid, particularly preferred being palmitoleic, oleic and gondoic acid.

The molar ratio between the fatty acid(s) and the phospholipid(s) forming the stabilizing envelope of the microvesicles is of at least 60/40 or higher, preferably 70/30 or higher, more preferably 75/25 or higher and even more preferably 78/22 or higher. Preferably, the molar ratio shall not be higher than 95/5, more preferably 90/10.

According to the present invention, the microvesicles' envelope further comprises a phospholipid. The term phospholipid is intended to encompass any amphiphilic phospholipid compound, the molecules of which are capable of forming a stabilizing film of material (typically in the form of a mono-molecular layer) at the gas-water boundary interface in the final microbubbles suspension.

Amphiphilic phospholipid compounds typically contain at least one phosphate group and at least one, preferably two, lipophilic long-chain hydrocarbon group.

Examples of suitable phospholipids include esters of glycerol with one or preferably two (equal or different) residues of fatty acids and with phosphoric acid, wherein the phosphoric acid residue is in turn bound to a hydrophilic group, such a, for instance, choline (phosphatidylcholines—PC), serine (phosphatidylserines—PS), glycerol (phosphatidylglycerols—PG), ethanolamine (phosphatidylethanolamines—PE), inositol (phosphatidylinositol). Esters of phospholipids with only one residue of fatty acid are generally referred to in the art as the "lyso" forms of the phospholipid or "lysophospholipids". Fatty acids residues present in the phospholipids are in general long chain aliphatic acids, typically containing from 12 to 24 carbon atoms, preferably from 14 to 22; the aliphatic chain may contain one or more unsaturations or is preferably completely saturated. Examples of suitable fatty acids included in the phospholipids are, for instance, lauric acid, myristic acid, palmitic acid, stearic acid, arachidic acid, behenic acid, oleic acid, linoleic acid, and linolenic acid. Preferably, saturated fatty acids such as myristic acid, palmitic acid, stearic acid and arachidic acid are employed.

Further examples of phospholipid are phosphatidic acids, i.e. the diesters of glycerol-phosphoric acid with fatty acids; sphingolipids such as sphingomyelins, i.e. those phosphatidylcholine analogs where the residue of glycerol diester with fatty acids is replaced by a ceramide chain; cardiolipins, i.e. the esters of 1,3-diphosphatidylglycerol with a fatty acid; glycolipids such as gangliosides GM1 (or GM2) or cerebrosides; glucolipids; sulfatides and glycosphingolipids.

As used herein, the term phospholipids includes either naturally occurring, semisynthetic or synthetically prepared products that can be employed either singularly or as mixtures.

Examples of naturally occurring phospholipids are natural lecithins (phosphatidylcholine (PC) derivatives) such as, typically, soya bean or egg yolk lecithins.

Examples of semisynthetic phospholipids are the partially or fully hydrogenated derivatives of the naturally occurring lecithins. Preferred phospholipids are fatty acids di-esters of phosphatidylcholine, ethylphosphatidylcholine, phosphatidylglycerol, phosphatidic acid, phosphatidylethanolamine, phosphatidylserine, phosphatidylinositol or of sphingomyelin.

Examples of preferred phospholipids are, for instance, dilauroyl-phosphatidylcholine (DLPC), dimyristoyl-phosphatidylcholine (DMPC), dipalmitoyl-phosphatidylcholine (DPPC), diarachidoyl-phosphatidylcholine (DAPC), distearoyl-phosphatidylcholine (DSPC), dioleoyl-phosphatidylcholine (DOPC), 1,2 Distearoyl-sn-glycero-3-Ethylphosphocholine (Ethyl-DSPC), dipentadecanoyl-phosphatidylcholine (DPDPC), 1-myristoyl-2-palmitoyl-phosphatidylcholine (MPPC), 1-palmitoyl-2-myristoyl-phosphatidylcholine (PMPC), 1-palmitoyl-2-stearoyl-phosphatidylcholine (PSPC), 1-stearoyl-2-palmitoyl-phosphatidylcholine (SPPC), 1-palmitoyl-2-oleylphosphatidylcholine (POPC), 1-oleyl-2-palmitoyl-phosphatidylcholine (OPPC), dilauroyl-phosphatidylglycerol (DLPG) and its alkali metal salts, diarachidoylphosphatidyl-glycerol (DAPG) and its alkali metal salts, dimyristoylphosphatidylglycerol (DMPG) and its alkali metal salts, dipalmitoylphosphatidylglycerol (DPPG) and its alkali metal salts, distearoylphosphatidyl-glycerol (DSPG) and its alkali metal salts, dioleoyl-phosphatidylglycerol (DOPG) and its alkali metal salts, dimyristoyl phosphatidic acid (DMPA) and its alkali metal salts, dipalmitoyl phosphatidic acid (DPPA) and its alkali metal salts, distearoyl phosphatidic acid (DSPA), diarachidoylphosphatidic acid (DAPA) and its alkali metal salts, dimyristoyl-phosphatidylethanolamine (DMPE), dipalmitoylphosphatidylethanolamine (DPPE), distearoyl phosphatidylethanolamine (DSPE), dioleylphosphatidyl-ethanolamine (DOPE), diarachidoylphosphatidyl-ethanolamine (DAPE), dilinoleylphosphatidylethanolamine (DLPE), dimyristoyl phosphatidylserine (DMPS), diarachidoyl phosphatidylserine (DAPS), dipalmitoyl phosphatidylserine (DPPS), distearoylphosphatidylserine (DSPS), dioleoylphosphatidylserine (DOPS), dipalmitoyl sphingomyelin (DPSP), and distearoylsphingomyelin (DSSP), dilauroyl-phosphatidylinositol (DLPI), diarachidoylphosphatidylinositol (DAPI), dimyristoylphosphatidylinositol (DMPI), dipalmitoylphosphatidylinositol (DPPI), distearoylphosphatidylinositol (DSPI), dioleoyl-phosphatidylinositol (DOPI).

Phospholipids may also be modified by linking a hydrophilic polymer thereto, such as polyethyleneglycol (PEG) or polypropyleneglycol (PPG), thereto. Polymer-modified phospholipids include for instance "pegylated phospholipids", i.e. phospholipids bound to a PEG polymer. Examples of pegylated phospholipids are pegylated phosphatidylethanolamines ("PE-PEGs" in brief) i.e. phosphatidylethanolamines where the hydrophilic ethanolamine moiety is linked to a PEG molecule of variable molecular weight (e.g. from 300 to 20000 daltons, preferably from 500 to 5000 daltons), such as DPPE-PEG (or DSPE-PEG, DMPE-PEG, DAPE-PEG or DOPE-PEG). For example, DPPE-PEG2000 refers to DPPE having attached thereto a PEG polymer having a mean average molecular weight of about 2000.

Particularly preferred phospholipids are DAPC, DSPC, DPPC, DMPA, DPPA, DSPA, DMPG, DPPG, DSPG, DMPS, DPPS, DSPS and Ethyl-DSPC. Most preferred are DPPG, DPPS and DSPC.

Mixtures of phospholipids can also be used, such as, for instance, mixtures of DPPE and/or DSPE (including pegylated derivates), DPPC, DSPC and/or DAPC with DSPS, DPPS, DSPA, DPPA, DSPG, DPPG, Ethyl-DSPC and/or Ethyl-DPPC.

According to the invention, the amount of phospholipids in the stabilizing envelope is of less than 50% by weight of the total weight of the components forming the envelope, preferably less than 40%.

The antigen is covalently bound to a component of the stabilizing envelope of the microbubble according to conventional methods, in particular by covalently binding the antigen to an amphiphilic component forming the stabilizing envelope of the microbubble (in brief "envelope-forming component"). Said component can be selected among those previously illustrated, particularly preferred being phospholipids, in particular phosphatidylethanolamines (e.g. DSPE or DPPE). The antigen is preferably linked directly to the envelope-forming component, e.g. by means of a covalent bond involving reactive groups contained in the respective components, thus obtaining a construct comprising the antigen linked to the envelope-forming. As a matter of fact, it has been observed that by avoiding the use of a PEG linker for binding the antigen to the phospholipid (and, more in general, by using microvesicles substantially devoid of pegylated phospholipids in their stabilizing envelope) more pronounced immune responses can be obtained.

The reacting components may either contain the desired reactive groups or can be modified ("functionalized") according to conventional techniques to include the desired reactive group into the component.

For instance, if one of the two reacting components includes a reactive amino group, it can be reacted with the other component containing a suitable corresponding reactive moiety, such as an isothiocyanate group (to form a thiourea bond), a reactive ester (to form an amide bond), or an aldehyde group (to form an imine bond, which may be reduced to an alkylamine bond). Alternatively, if one of the two reacting components includes a reactive thiol group, suitable complementary reactive moieties on the other component may include haloacetyl derivatives, maleimides (to form a thioether bond) or a mixed disulfide comprising a sulphide in the form of a 2-pyridylthio group which upon reaction with a thiol derived from the thiol-bearing component results in the formation of a stable disulfide bond between the two components. Furthermore, if one of the two reacting components includes a reactive carboxylic group, suitable reactive moieties on the other component can be amines and hydrazides (to form amide or N-acyl, N'-alkylhydrazide functions). For example, a maleimide-derivatized phospholipid (e.g. phosphatidylethanolamine) can be prepared which is then reacted with a mercaptoacetylated antigen (e.g. a protein), previously incubated in a deacetylation solution.

Antigens, in particular vaccine antigens, which can be covalently bound to a gas-filled microvesicle in a system according to the invention include, but are not limited to natural, recombinant or synthetic products, as well as fragments thereof. Suitable antigens, in particular vaccine antigens, may include, for instance: allergenic antigens derived from or associated with, for instance, plant pollen, insect venom (e.g. Phospholipase A2 from *Apis mellifera*), food, animal dander, dust mites; viral antigens derived from or associated with, for instance, adenovirus, alphavirus, corona virus, cytomegalovirus, distemper, enterovirus species, Epstein Barr virus, flavivirus, hepatitis A, hepatitis B, hepatitis E, herpes species, HIV-1, HIV-2, HTLV 1, human retrovirus species, influenza, lymphocytic choriomeningitis virus, measles, papilloma virus, parainfluenza virus, paramyxovirus, parovirus, poliomyelitis, polyoma tumor virus, rabies, reovirus, togavirus, varicella-zoster virus; bacterial antigens derived from or associated with, for instance, *Bordetella pertussis, Borrelia burgdirferi, brucella* species, *chlamydia, anaplasmataceae enterobacter* species, *Escherichia coli, haemophilus* species, *Helicobacter pylori, Klebsiella pneumonia, legionellosis, menigococcus, mycobacteria* species, *Neisseria gonorrhoeae, pasturella* species, *pneumococci, pseudomonas, ricksettia, salmonella* species, *staphylococci, streptococci, Treponema palladium, vivrio, Yersinia enterocolitica*; fungal antigen derived from or associated with, for instance, *Coccidioides immiti, histoplasmin, trichophytin, dermatophytin, Apergillus fumigatus, Candida albicans, Cladosporium herbarum, Pneumocystis jirovecii*; toxin-derived antigen, derived from or associated with, for instance, *Bordetella pertussis, Clostridium botulinum, Clostridium tetani, Clostridium tetani*; parasitic antigens, derived from or associated with, for instance, *coccidian, filarial nematodes, leishmania, plasmodium, sarcocystis, schistosoma, taenia, Toxoplasma gondii, Trichinella spiralis, Trichomonas vaginalis*, trypanosomes; self antigens, such as those responsible, for instance, for diabetes mellitus type 1, coeliac disease, systemic lupus erythermatosis, rheumatoid arthritis, Grave's Disease, Idiopathic thrombocytopenic purpura, Sjögren's syndrome, chronic lymphocytic thyroiditis; or tumor antigens such as, for instance, tyrosinase, Melan-A/MART-1 or other melanoma-associated antigen, cancer/testis antigens, carcinogenic embryonic antigen, polymorphic epithelial mucins, epithelial cellular adhesion molecule, human papilloma virus, prostate-specific agent or alpha-fetoprotein.

The amount of antigen bound to the microvesicle's envelope may vary depending from the type of antigen and from the type of immunomodulation which has to be induced in the patient. For instance, the antigen may vary from about 0.1% to about 10% by moles, with respect to the total amount of components forming the microvesicle's envelope. Preferably, said amount may vary from about 0.2% to about 5% by moles and even more preferably from about 0.5% to about 2% by moles.

The gas-filled microvesicles may optionally comprise an immunomodulating compound (adjuvant), preferably amphiphilic, for increasing/modifying the adjuvant effect of the microvesicles. Examples of adjuvants are disclosed, for instance, by Reed S G, Bertholet S, Coler R N et al., "New horizons in adjuvants for vaccine development. Trends in immunology 2008", 30(1): 23-32; or by Wilson-Welder J H, Torres M, Kipper M J et al., "Vaccine Adjuvants: Current challenges and Future Approaches", J Pharm Sci 2009; 98(4):1278-1316.

The amount of immunomodulating adjuvant in the stabilizing envelope may vary from about 0.1% to about 20% by mole, preferably from about 0.5% to about 15% and even more preferably from about 1% to about 10% by mole (with respect to the total molar amount of the materials forming the stabilizing envelope).

Other excipients or additives may be present either in the dry formulation of the microbubbles or may be added together with the aqueous carrier used for the reconstitution thereof, without necessarily being involved (or only partially involved) in the formation of the stabilizing envelope of the microbubble. These include pH regulators, osmolality adjusters, viscosity enhancers, emulsifiers, bulking agents, etc. and may be used in conventional amounts. For instance compounds like polyoxypropylene glycol and polyoxyethylene glycol as well as copolymers thereof can be used. Examples of viscosity enhancers or stabilizers are compounds selected from linear and cross-linked poly- and oligo-saccharides, sugars and hydrophilic polymers such as polyethylene glycol.

As the preparation of gas-filled microbubbles may involve a freeze drying or spray drying step, it may be advantageous to include in the formulation a lyophilization additive, such as an agent with cryoprotective and/or lyoprotective effect and/or a bulking agent, for example an amino-acid such as glycine; a carbohydrate, e.g. a sugar such as sucrose, mannitol, maltose, trehalose, glucose, lactose or a cyclodextrin, or a polysaccharide such as dextran, chitosan and its derivatives (for example: carboxymethyl chitosan, trimethyl chitosan); or a polyoxyalkyleneglycol such as polyethylene glycol.

The microbubbles of a composition according to the invention can be produced according to any known method in the art. Typically, the manufacturing method involves the preparation of a dried powdered material comprising an amphiphilic material as indicated above, preferably by lyophilization (freeze drying) of an aqueous or organic suspension comprising said material.

For instance, as described in WO 91/15244, film-forming amphiphilic compounds can be first converted into a lamellar form by any method employed for formation of liposomes. To this end, an aqueous solution comprising the film forming lipids and optionally other additives (e.g. viscosity enhancers, non-film forming surfactants, electrolytes etc.) can be submitted to high-speed mechanical homogenisation or to sonication under acoustic or ultrasonic frequencies, and then freeze dried to form a free flowing powder which is then stored in the presence of a gas. Optional washing steps, as disclosed for instance in U.S. Pat. No. 5,597,549, can be performed before freeze drying.

According to an alternative embodiment (described for instance in U.S. Pat. No. 5,597,549) a film forming compound and a hydrophilic stabiliser (e.g. polyethylene glycol, polyvinyl pyrrolidone, polyvinyl alcohol, glycolic acid, malic acid or maltol) can be dissolved in an organic solvent (e.g. tertiary butanol, 2-methyl-2-butanol or $C_2Cl_4F_2$) and the solution can be freeze-dried to form a dry powder.

Preferably, as disclosed for instance in International patent application WO2004/069284, a phospholipid (selected among those cited above and including at least one of the above-identified charged phospholipids) and a lyoprotecting agent (such as those previously listed, in particular carbohydrates, sugar alcohols, polyglycols, polyoxyalkylene glycols and mixtures thereof) can be dispersed in an emulsion of water with a water immiscible organic solvent (e.g. branched or linear alkanes, alkenes, cyclo-alkanes, aromatic hydrocarbons, alkyl ethers, ketones, halogenated hydrocarbons, perfluorinated hydrocarbons or mixtures thereof) under agitation. The emulsion can be obtained by submitting the aqueous medium and the solvent in the presence of at least one phospholipid to any appropriate emulsion-generating technique known in the art, such as, for instance, sonication, shaking, high pressure homogenization, micromixing, membrane emulsification, high speed stirring or high shear mixing. For instance, a rotor-stator homogenizer can be employed, such as Polytron® PT3000. The agitation speed of the rotor-stator homogenizer can be selected depending from the components of the emulsion, the volume of the emulsion, the relative volume of organic solvent, the diameter of the vessel containing the emulsion and the desired final diameter of the microdroplets of solvent in the emulsion. Alternatively, a micromixing technique can be employed for emulsifying the mixture, e.g. by introducing the organic solvent into the mixer through a first inlet (at a flow rate of e.g. 0.05-5 mL/min), and the aqueous phase a second inlet (e.g. at a flow rate of 2-100 mL/min). Depending on the emulsion technique, the organic solvent can be introduced gradually during the emulsification step or at once before starting the emulsification step. Alternatively the aqueous medium can be gradually added to the water immiscible solvent during the emulsification step or at once before starting the emulsification step. Preferably, the phospholipid is dispersed in the aqueous medium before this latter is admixed with the organic solvent. Alternatively, the phospholipid can be dispersed in the organic solvent or it may be separately added the aqueous-organic mixture before or during the emulsification step. The so obtained microemulsion, which contains microdroplets of solvent surrounded and stabilized by the phospholipid material (and optionally by other amphiphilic film-forming compounds and/or additives), is then lyophilized according to conventional techniques to obtain a lyophilized material, which is stored (e.g. in a vial in the presence of a suitable gas) and which can be reconstituted with an aqueous carrier to finally give a gas-filled microbubbles suspension where the dimensions and size distribution of the microbubbles are substantially comparable with the dimensions and size distribution of the suspension of microdroplets.

A further process for preparing gas-filled microbubbles comprises generating a gas microbubble dispersion by submitting an aqueous medium comprising a phospholipid (and optionally other amphiphilic film-forming compounds and/or additives) to a controlled high agitation energy (e.g. by means of a rotor stator mixer) in the presence of a desired gas and subjecting the obtained dispersion to lyophilisation to yield a dried reconstitutable product. An example of this process is given, for instance, in WO97/29782, here enclosed by reference.

Spray drying techniques (as disclosed for instance in U.S. Pat. No. 5,605,673) can also be used to obtain a dried powder, reconstitutable upon contact with physiological aqueous carrier to obtain gas-filled microbubbles.

The dried or lyophilized product obtained with any of the above techniques will generally be in the form of a powder or a cake, and can be stored (e.g. in a vial) in contact with the desired gas. The product is readily reconstitutable in a suitable physiologically acceptable aqueous liquid carrier, which is typically injectable, to form the suspension of gas-filled microbubbles, upon gentle agitation of the vial. Suitable physiologically acceptable liquid carriers are sterile water, aqueous solutions such as saline (which may advantageously be balanced so that the final product for injection is not hypotonic), or solutions of one or more tonicity adjusting substances such as salts or sugars, sugar alcohols, glycols or other non-ionic polyol materials (eg. glucose, sucrose, sorbitol, mannitol, glycerol, polyethylene glycols, propylene glycols and the like), chitosan derivatives, such as carboxymethyl chitosan, trimethyl chitosan or gelifying compounds, such as carboxymethylcellulose, hydroxyethyl starch or dextran.

According to an embodiment of the invention, the construct comprising the antigen (i.e. an antigen/envelope-forming-component construct or an antigen/spacer/envelope-forming-component construct) can be admixed as such with the other components of the formulation, so to be incorporated into the stabilizing envelope upon reconstitution of the freeze-dried material obtained according to any of the above preparation methods.

Alternatively, the construct can be admixed as a suitably functionalized intermediate (e.g. a functionalized envelope-forming component such as a maleimide-containing phosphatidylethanolamine) to the initial formulation, to produce a freeze-dried material containing said intermediate; the antigen, containing a suitable complementary reactive moiety (e.g. thiol), can then be linked, by reacting the respective reactive moieties, to the intermediate compound already incorporated in the envelope of the reconstituted microbubbles.

In the case of the process disclosed in WO2004/069284, the construct containing the antigen can also be admixed with the components of the initial mixture, undergoing to the emulsion and lyophilisation steps. Alternatively, a micellar suspension containing the construct can be separately prepared and subsequently added to the already formed emulsion (containing the other film-forming components), preferably under heating. As above, instead of the formed construct, a functionalized intermediate can alternatively be used, which can then be reacted at any step of the process (e.g. in the emulsion phase or upon reconstitution of the lyophilized compound) with an antigen containing a complementary reactive moiety. According to an embodiment, a functionalized envelope-forming component (or envelope-forming/spacer intermediate construct) is added as a micellar suspension to the formed emulsion, under agitation. A compound comprising the antigen (containing the complementary reactive moiety) is then added to the obtained emulsion.

For example, a micellar suspension of a maleimide derivative of an envelope-forming component can be added to the formed emulsion of film forming components. Then, a solution of a mercaptoacetylated antigen is added to the emulsion, under gentle agitation, before lyophilization of the emulsion. Alternatively, the emulsion containing the maleimide derivative of the envelope-forming component is lyophilized and then the unprotected antigen is subsequently added to the reconstituted suspension of gas-filled microvesicles.

Any biocompatible gas, gas precursor or mixture thereof may be employed to fill the above microvesicles (hereinafter also identified as “microvesicle-forming gas”).

The gas may comprise, for example, air; nitrogen; oxygen; carbon dioxide; hydrogen; nitrous oxide; a noble or inert gas such as helium, argon, xenon or krypton; a low molecular weight hydrocarbon (e.g. containing up to 7 carbon atoms), for example an alkane such as methane, ethane, propane, butane, isobutane, pentane or isopentane, a cycloalkane such as cyclobutane or cyclopentane, an alkene such as propene, butene or isobutene, or an alkyne such as acetylene; an ether; a ketone; an ester; halogenated gases, preferably fluorinated gases, such as or halogenated, fluorinated or perfluorinated low molecular weight hydrocarbons (e.g. containing up to 7 carbon atoms); or a mixture of any of the foregoing. Where a halogenated hydrocarbon is used, preferably at least some, more preferably all, of the halogen atoms in said compound are fluorine atoms.

Fluorinated gases are preferred, in particular perfluorinated gases. Fluorinated gases include materials which contain at least one fluorine atom such as, for instance fluorinated hydrocarbons (organic compounds containing one or more carbon atoms and fluorine); sulfur hexafluoride; fluorinated, preferably perfluorinated, ketones such as perfluoroacetone; and fluorinated, preferably perfluorinated, ethers such as perfluorodiethyl ether. Preferred compounds are perfluorinated gases, such as $SF_6$ or perfluorocarbons (perfluorinated hydrocarbons), i.e. hydrocarbons where all the hydrogen atoms are replaced by fluorine atoms, which are known to form particularly stable microbubble suspensions, as disclosed, for instance, in EP 0554 213.

The term perfluorocarbon includes saturated, unsaturated, and cyclic perfluorocarbons. Examples of biocompatible, physiologically acceptable perfluorocarbons are: perfluoroalkanes, such as perfluoromethane, perfluoroethane, perfluoropropanes, perfluorobutanes (e.g. perfluoro-n-butane, optionally in admixture with other isomers such as perfluoro-isobutane), perfluoropentanes, perfluorohexanes or perfluoroheptanes; perfluoroalkenes, such as perfluoropropene, perfluorobutenes (e.g. perfluorobut-2ene) or perfluorobutadiene; perfluoroalkynes (e.g. perfluorobut-2-yne); and perfluorocycloalkanes (e.g. perfluorocyclobutane, perfluoromethylcyclobutane, perfluorodimethylcyclobutanes, perfluorotrimethylcyclobutanes, perfluorocyclopentane, perfluoromethylcyclopentane, perfluorodimethylcyclopentanes, perfluorocyclohexane, perfluoromethylcyclohexane and perfluorocycloheptane). Preferred saturated perfluorocarbons include, for example, $CF_4$, $C_2F_6$, $C_3F_8$, $C_4F_8$, $C_4F_{10}$, $C_5F_{12}$ and $C_6F_{12}$.

It may also be advantageous to use a mixture of any of the above gases in any ratio. For instance, the mixture may comprise a conventional gas, such as nitrogen, air or carbon dioxide and a gas forming a stable microbubble suspension, such as sulfur hexafluoride or a perfluorocarbon as indicated above. Examples of suitable gas mixtures can be found, for instance, in WO 94/09829, which is herein incorporated by reference. The following combinations are particularly preferred: a mixture of gases (A) and (B) in which the gas (B) is a fluorinated gas, selected among those previously illustrated, including mixtures thereof, and (A) is selected from air, oxygen, nitrogen, carbon dioxide or mixtures thereof. The amount of gas (B) can represent from about 0.5% to about 95% v/v of the total mixture, preferably from about 5% to 80%.

Particularly preferred gases are $SF_6$, $C_3F_8$, $C_4F_{10}$ or mixtures thereof, optionally in admixture with air, oxygen, nitrogen, carbon dioxide or mixtures thereof.

In certain circumstances it may be desirable to include a precursor to a gaseous substance (i.e. a material that is capable of being converted to a gas in vivo). Preferably the gaseous precursor and the gas derived therefrom are physiologically acceptable. The gaseous precursor may be pH-activated, photo-activated, temperature activated, etc. For example, certain perfluorocarbons may be used as temperature activated gaseous precursors. These perfluorocarbons, such as perfluoropentane or perfluorohexane, have a liquid/gas phase transition temperature above room temperature (or the temperature at which the agents are produced and/or stored) but below body temperature; thus, they undergo a liquid/gas phase transition and are converted to a gas within the human body.

As mentioned previously, the microvesicles of the invention are particularly useful as vaccine and/or immunomodulating formulations.

The Applicant has observed that the microvesicles of the invention are particularly effective in the uptake by antigen-presenting cells, in particular dendritic cells ("DC" in the following), as compared to microvesicles where the antigen is not covalently bound thereto (e.g. encapsulated or adsorbed). As observed by the Applicant, said increased uptake results in a higher production of specific antibodies against the covalently-bound antigen, as well as an increase in antigen-specific T cell responses.

In view of their advantageous adjuvant effect on promoting/modulating immune responses, the microvesicles of the invention can be used for effectively administering any of the previously listed (vaccine) antigens covalently bound thereto. Administration of microvesicles can be performed, for instance, by subcutaneous, intradermal, transdermal, intramuscular or intravenous injections or by mucosal routes, such as oral, sublingual, nasal, intra-bladder, vaginal or rectal delivery. Administrations, up to e.g. a total number of five, can be done at intervals comprised, for instance, between 1 week and 6 months. The composition is preferably administered in the form of an aqueous suspension of gas-filled microvesicles. Alternatively, the composition can be administered as a lyophilisate or as a gel solution.

An example of a protocol of injection/immunization is presented in the working examples herein.

The microvesicles of the invention can thus be used in any medical treatment comprising or inducing a modulation of the immune response in a patient in need thereof, in particular a treatment for modulating the immune response in a patient in need thereof. Typically, the treatment comprises vaccination of the patient.

For instance, the immunomodulating treatment may include treatment of infections (typically bacterial, viral, parasitic and/or fungal infections such as, for instance, malaria, meningitis, measles, AIDS, flu (influenza), cholera, listeriosis or salmonellosis), treatment of tumors (such as, for instance, breast, prostate, lung, ovarian, bladder or esophageal cancer, sarcoma or melanoma) and treatments of allergies, including e.g. environmental or nutritional allergies (such as, for instance, pollen, bee venom, dust mite, latex, milk (lactose), peanuts and/or eggs (albumen) allergies.)

The following examples will help to further illustrate the invention.

EXAMPLES

The following materials and abbreviations are used in the subsequent examples:

| | |
|---|---|
| DSPC | Distearoylphosphatidylcholine (Genzyme) |
| Palmitic acid | Palmitic acid, Hexadecanoic acid (Fluka) |
| DSPE-PEG2000-mal | Distearoylphosphatidylethanolamine modified with PEG2000-maleimide (Avanti Polar lipids) |
| DPPE-MPB | 1,2-dipalmitoyl-sn-glycero-3-phosphoethanol-amine-N-[4-(p-maleimidophenyl)butyramide |
| Traut reagent | 2-Iminothiolane hydrochloride (Pierce) |
| PEG4000 | Polyethyleneglycol 4000S from Clariant |
| Cyclooctane | Fluka |
| Ellman's reagent | 5,5'-Dithio-bis-(2-nitrobenzoic acid), (Pierce) |
| OVA | Albumin from chicken egg white grade V (Sigma) |
| PBS | Phosphate buffer saline (Büchsel AG) |
| CD3 (PE*Cy7-conjugated) | BD Biosciences |
| CD4 (PE-conjugated) | BD Biosciences |
| CD8 (Alexa647-conjugated) | BD Biosciences |
| CD40 (FITC-conjugated) | BD Biosciences |
| DAPI | 4',6'-diamidino-2-phenylindole (Invitrogen) |
| CFSE | Carboxyfluorescein succinimidylester (Sigma) |
| TNF-α ELISA kit | BioLegend |
| IFN-γ ELISA kit | BioLegend |
| IL-2 ELISA kit | BioLegend |
| IL-10 ELISA kit | BioLegend |
| IL-4 ELISA kit | BioLegend |
| IL-5 ELISA kit | BioLegend |
| IL-13 ELISA kit | eBioscience |
| DC2.4 | Dendritic cell line; obtained from K. L. Rock (University of Massachusetts Medical School, Worcester, MA) |
| IgG (HRP conjugated) | Sigma-Aldrich |
| IgG1 (biotin conjugated) | Invitrogen |
| IgG2a (biotin conjugated) | Invitrogen |
| Extravidin-HRP | Sigma-Aldrich |
| TMB (HRP substrate) | BD Bioscience |

Example 1

Preparation of Gas-Filled Microvesicles Comprising a Covalently-Bound Antigen (OVA)

a) Thiolation of OVA

OVA (6 mg-133 nmoles) was dissolved in PBE (Phosphate buffer 25 mM, 150 mM saline, 1 mM EDTA, pH 8) to obtain a solution at 20 mg/mL. A solution of Traut reagent (2 mg/mL-14.5 mM) was prepared in PBE and 92 µL of this solution (10 equ.) were added to the OVA solution. The resulting mixture was incubated at room temperature for 1 h under stirring. This solution was spun through a spin-column (Zeba spin column 2 mL, Pierce, #89890) equilibrated in PBE. The final volume of the solution was of about 390 µL.

The final OVA concentration (measured by UV at 280 nm) was about 300 nmol./mL

The thiolated OVA solution was used immediately after purification to limit possible oxidation of the thiols.

b) Preparation of Microvesicles with Covalently Bound OVA:

Four preparations of gas-filled microvesicles were prepared with the following methodology, namely preparations A1 and A2 according to the invention and comparative preparations B1 and B2. Type and amounts of components in the respective preparations are identified in Table 1 below.

b1) For reparations A1 and B1:

DSPE-PEG-maleimide (2.2 mg-7.47 µmoles) was dissolved in phosphate buffer 100 mM pH 6 (0.2 mL) at 45° C. by stirring (vortex) to obtain a clear solution.

20 mg of a mixture of DSPC/Palmitic acid (molar ratio indicated in table 1) were dissolved in cyclooctane (1.6 mL) at 70° C. Separately, the aqueous solution prepared above (0.2 mL) was added to 19.8 mL of PEG4000 10% solution. The organic phase containing the phospholipids was then added to the aqueous phase and emulsified by using a high speed homogenizer (Polytron PT3100, 1 min at 11'000 rpm). The emulsion was divided in 10 mL fractions in PP tubes (Falcon-15 mL).

b2) for Preparations A2 and B2:

DPPE-MPB (4.2 mg-4.39 µmoles) was admixed with 20 mg of a mixture of DSPC/Palmitic acid (molar ratio indicated in table 1) and dissolved in ethanol at 60° C. by stirring (vortex) to obtain a clear solution. The solvent was evaporated under nitrogen and the residue dried under vacuum overnight.

The dried residue was dissolved in cyclooctane (1.6 mL) at 70° C., 20 ml of PEG4000 10% were added to the organic phase and the mixture was emulsified by using a high speed homogenizer (Polytron PT3100, 1 min at 11'000 rpm). The emulsion was divided in 10 mL fractions in PP tubes (Falcon-15 mL).

Thiolated OVA (78 nmoles) was added to 10 mL of the emulsion obtained according to steps b1 or b2 above and the resulting mixture was agitated at 22° C. for 2 hours and 30 min. The obtained emulsion was finally diluted twice with 10% PEG4000 solution and sampled in DIN4R vials (500 µL per vial). Vials were frozen at −50° C. for 2 h (Christ Epsilon lyophilizer), then freeze-dried at −25° C. and 0.2 mBar for 12 h. The lyophilized product was then exposed to an atmosphere containing 35% of perfluoro-n-butane and 65% of air.

1 mL of saline (150 mM NaCl) was added to the vial for dispersing the freeze-dried precursor and reconstituting the microvesicle suspension by gentle hand shaking. In the subsequent examples, the volume of saline for reconstitution is adapted to obtain the desired concentration of antigen as required by the specific experiment.

The compositions and characteristics of the four preparations are illustrated in table 1 below. In particular, the microvesicles in preparations A1 and A2 according to the invention comprise a 80/20 molar ratio between fatty acids and phospholipids in the stabilizing envelope, while the microvesicles in comparative preparations B1 and B2 comprise a 20/80 molar ratio between fatty acids and phospholipids in the stabilizing envelope, as in the working example of the above cited WO 2012/085072; furthermore, in preparation A1 and respective comparative preparation B1 the antigen is linked to the phospholipid through a pegylated linker, while in preparation A2 and respective comparative preparation B2 the antigen is directly linked to the phospholipid.

TABLE 1

Composition of microvesicles preparations

| Preparation | Components (molar %) | | | | Amount of OVA in the vial (µg) |
|---|---|---|---|---|---|
| | DSPC | PA | DSPE-PEG-Mal | DPPE-MPB | |
| A1 | 19.5 | 78 | 2.5 | 0 | 110 |
| A2 | 19 | 76.2 | 0 | 4.8 | 90.8 |
| B1 (comp) | 78 | 19.5 | 2.5 | 0 | 97.8 |
| B2 (comp) | 76.2 | 19 | 0 | 4.8 | 87.1 |

DSPC = distearoyl-phosphatidyl-choline;
PA = palmitic acid;
DSPE-PEG-Mal = distearoyl-phosphatidyl-ethanolamine;
DPPE-MPB = maleimidophenyl-butyryl-dipalmitoyl-phosphatidylethanolamine Example 2

In-Vitro Activation of Murine DC: Comparison Between Microvesicles Preparation A1 and Comparative B1

Spleen-derived mouse DC2.4 cells were maintained in complete RPMI medium. They were incubated in poly-L-lysine-coated mini tray culture plates in complete RPMI medium. 5 µl of microvesicle preparations A1 or B1 (reconstituted at a dilution such to obtain a ratio of 1000 microvesicles:1 DC) were then added to the wells and the culture plates were inverted and incubated upside-down at 37° C. for 24 h. TNF-alpha in culture supernatant was quantified by Enzyme-Linked ImmunoSorbent Assay (ELISA). Cells were blocked with mAb against CD16/32, stained with monoclonal antibody against CD40 and analyzed with a Gallios flow cytometer and FlowJo software (Tree Star Inc, Ashland, Oreg.).

The results of Table 2 show that preparations according to the invention (A1) possesses a superior ability to induce cell activation as compared to comparative preparations with low fatty acid content in the envelope (B1). In particular, it can be observed that TNF-alpha production of DC obtained after incubation with microvesicles of preparation A1 is doubled compared to incubation with microvesicles of preparation B1. Similarly, CD40 expression by the DC is higher after incubation with preparation A1 than after incubation with comparative preparation B1.

TABLE 2

In-vitro activation of murine DC

| | Medium (neg. control) | LPS (pos. control) | Prep. A1 | Prep. B1 (comp) |
|---|---|---|---|---|
| TNF-alpha (pg/mL) | 47 | 1972 | 979 | 472 |
| CD40 (fluorescence) | 1564 | 4896 | 2295 | 1852 |

Example 3

Comparison of Short-Term Immune Responses Between Preparations A1 and A2 and Respective Comparative Preparations B1 and B2

Mice were immunized subcutaneously at the base of the tail with 100 µl of different microvesicles preparations (A1, A2, B1 or B2; the precursors in the vials of Example 1 having been reconstituted with a volume of saline such to provide a concentration of 4.5 µg of OVA per 100 µl of suspension). Endotoxin levels were measured by Limulus Amebocyte Lysate assay and found to be below 1 endotoxin unit (EU) per μg of OVA. Three administrations at two-week intervals were performed and spleens were collected 14 d after the last injection. The presence and titers of OVA-specific antibodies in sera were determined by ELISA according to the following protocol. Briefly, Maxisorb plates (Nunc) were coated with 10 μg/mL OVA, blocked with PBS-0.05% Tween 20-1% BSA and washed before addition of titrated doses of sera. Following overnight incubation at 4° C., plates were washed and the presence of OVA-specific IgG was assessed by incubation with HRP-coupled anti-IgG antibody. Following washing, HRP substrate was added and the reaction was stopped after a few minutes with 1M H2SO4 and OD 450 nm was measured. Based on the titration curves obtained (sera dilutions (agonist) vs. OD 450 nm (response)), a sigmoid fitting curve was generated. The serum dilution (titer) giving half maximal OD 450 nm for each curve was then calculated (EC50), that enables a comparison of each condition tested. Splenocytes were seeded into round-bottom 96-well plates at $4 \cdot 10^5$ cells/well and incubated with either medium alone, OVA (100 μg/mL) or concanavalin A (1.5 μg/mL) as positive control and incubated. Cell culture supernatants were collected after 72 h of incubation and analyzed for the presence of IL-2, IFN-gamma, IL-10, IL-4 by Enzyme-Linked ImmunoSorbent Assay (ELISA).

Table 3 shows that both specific anti-OVA IgG1 and IgG2a were largely increased after short-term immunization with microvesicles preparations A1 compared with preparations B1 and B2. Immunization with preparation A2 produced higher levels of OVA-specific IgG1 when compared with preparations B1 or A2.

TABLE 3

Short-term immune responses: specific antibody production

| OVA specific antibodies Titer | Prep. A1 | Prep. B1 | Prep. A2 | Prep. B2 |
|---|---|---|---|---|
| IgG1 | 131926 | 67524 | 114498 | 63991 |
| IgG2A | 2399 | 535 | 496 | 890 |

Table 4 shows the cytokine measurement in culture supernatants from OVA-stimulated splenic cell suspensions from vaccinated Balb/c mice. The presence of microvesicles preparations A1 and A2 allowed to generate a more pronounced Th1-type of immune response (as reflected by the important production of IFN-gamma and IL-2 in splenocytes of immunized mice) with respect to respective comparative preparations B1 and B2; as observable from the results of Table 4, the Th1-type of immune response is further increased by preparations where the antigen is directly bound to the phospholipid (A2) with respect to preparations where the antigen is bound to the phospholipid via a PEG linker (A1). Production of IL-10 and IL-4 was similarly increased by the presence of preparations of the invention A1 and A2.

TABLE 4

Short-term immune responses: cytokine production by T-cells

| Cytokines (pg/ml) | Prep. A1 | Prep. B1 | Prep. A2 | Prep. B2 |
|---|---|---|---|---|
| IFN-gamma | 3478 | 1203 | 8419 | 2665 |
| IL-2 | 293 | 170 | 534 | 259 |

TABLE 4-continued

Short-term immune responses: cytokine production by T-cells

| Cytokines (pg/ml) | Prep. A1 | Prep. B1 | Prep. A2 | Prep. B2 |
|---|---|---|---|---|
| IL-10 | 1974 | 1046 | 2899 | 1810 |
| IL-4 | 446 | 137 | 458 | 116 |

Example 4

Comparison of Long-Term Persistence of T Cell Responses

Mice were immunized subcutaneously at the base of the tail with 100 μl of microvesicles preparations A2 or B1 (the vials of example 1 having been reconstituted with a volume of saline such to provide a concentration of 4.5 μg of OVA per 100 μl of suspension). Three administrations at two-week intervals were performed and blood and spleen were collected 14 days, 2 months and 6 months after the last injection. Splenic cell suspensions were analyzed as described in Example 3 for cytokine production. In addition, splenocytes were labeled with CFSE in PBS 0.1% BSA at 37° C. and then washed with cold PBS 5% fetal calf serum, before being seeded in 96-well plates.

Table 5 shows antigen-specific proliferation of splenic T cells from vaccinated BALB/c mice analyzed 14 days, 2 months and 6 months after the last injection of a preparation according to the invention (A2) or of a comparative preparation (B1). Both CD4 and CD8 T cells display important proliferative capacities both early (14 days) and 6 months post-vaccination. Proliferation of both CD4 and CD8 T cells was superior when mice were administered preparation A2 according to the invention.

The results of Table 6 shows the cytokine quantification in culture supernatants from OVA-stimulated splenic cell suspensions from BALB/c mice previously vaccinated with preparation A2 or B1. A sustained production of cytokines is observed the first 2 months post-immunization, except for IL-4. In all conditions, levels of cytokines tend to be higher after vaccination with preparation A2 as compared with preparation B1. Upon time, mice vaccinated with preparation A2 produced significantly more IL-2 and IFN-gamma, as compared to preparation B1.

TABLE 5

Long-term persistence of T cell responses

| | 14 days | | 2 months | | 6 months | |
|---|---|---|---|---|---|---|
| | Prep. B1 | Prep A2 | Prep. B1 | Prep A2 | Prep. B1 | Prep A2 |
| SI CD4 T cells | 6.7 | 12.3 | 11.4 | 17.3 | 6.9 | 11.4 |
| SI CD8 T cells | 10.0 | 17.0 | 10.0 | 17.8 | 9.5 | 16.6 |

TABLE 6

Long-term immune responses: cytokine quantification

| Cytokines (pg/ml) | 14 days Prep. B1 | Prep A2 | 2 months Prep. B1 | Prep A2 | 6 months Prep. B1 | Prep A2 |
|---|---|---|---|---|---|---|
| IFN-gamma | 1479 | 2982 | 2211 | 4262 | 387 | 915 |
| IL-2 | 613 | 955 | 438 | 1020 | 256 | 439 |
| IL-10 | 1711 | 2961 | 985 | 1191 | 301 | 483 |
| IL-4 | 78 | 111 | 31 | 71 | 23 | 31 |
| IL-5 | 1117 | 1611 | 1066 | 1288 | 433 | 750 |
| IL-13 | 2010 | 2587 | 1967 | 3564 | 600 | 1381 |

Example 5

Long-Term Vaccine-Induced Protection Against OVA-Lm Infection

Mice were immunized subcutaneously at the base of the tail with 100 µl of microvesicles preparations A2 or B1 (the vials of example 1 having been reconstituted with a volume of saline such to provide a concentration of 4.5 µg of OVA per 100 µl of suspension). Three administrations at two-week intervals were performed. 6 months after the last immunization a PBS solution of 50'000 colony forming units (CFU) of Recombinant *Listeria monocytogenes* stably expressing OVA (OVA-Lm) was injected intravenously. OVA-Lm burden in the spleen and liver were analyzed 4 days after infection. Spleens and livers in PBS-0.1% NP40 buffer were mashed through 70-µm cell strainers and serial dilutions were spread onto BHI agarose plates containing 200 µg/ml streptomycin and incubated for 24 h at 37° C. Bacterial counts are expressed as CFU/mg of spleen or liver. IFN-γ produced by splenic cell suspensions was quantified as described in Example 2.

As inferable from the data in Table 7, while mice vaccinated with comparative preparation B1 showed an increased ability to fight against infection with respect to those of the control group (without antigen), vaccination of mice with the preparation of the invention A2 led to a significant reduction of the bacterial load in the liver and spleen examined 4 days post-challenge with OVA-Lm. Mice displaying reduced bacterial loads (vaccinated with preparation A2) all survived infection, whereas 2 out 4 died in the preparation B1 vaccines within 4 days and 3 out 4 administered with the control without antigen died within four days. Partial protection correlated with the production of a substantial level of IFN-gamma by splenocytes obtained from mice vaccinated with the optimized preparation A2 (Table 7).

TABLE 7

Long-term vaccine-induced protection

| | Microvesicles without antigen (control) | Prep. B1 (Comp.) | Prep. A2 |
|---|---|---|---|
| CFU/mg in liver | $2.20 \cdot 10^6$ | $1.91 \cdot 10^6$ | $7.00 \cdot 10^5$ |
| CFU/mg in spleen | $2.87 \cdot 10^6$ | $2.37 \cdot 10^6$ | $6.90 \cdot 10^5$ |
| Splenocytes IFN-gamma production (pg/ml) | 170 | 3528 | 12020 |

The invention claimed is:

1. A pharmaceutical formulation comprising an aqueous suspension of gas-filled microvesicles with a stabilizing envelope, said stabilizing envelope comprising (a) an antigen covalently bound to an amphiphilic component forming said stabilizing envelope, (b) a phospholipid, and (c) a fatty acid, with a molar ratio between the phospholipid and the fatty acid lower than 25/75.

2. The pharmaceutical formulation according to claim 1, wherein said molar ratio is of 20/80 or lower.

3. The pharmaceutical formulation according to claim 1, wherein the phospholipid in the stabilizing envelope is less than 50% by weight with respect to total amount of components forming the stabilizing envelope.

4. The pharmaceutical formulation according to claim 1, wherein said antigen is present in a molar amount of from 0.1% to 10% in said stabilizing envelope.

5. The pharmaceutical formulation according to claim 1, wherein the gas-filled microvesicles contain a gas that comprises a fluorinated gas.

6. The pharmaceutical formulation according to claim 5, wherein said gas is in admixture with air or nitrogen.

7. The pharmaceutical formulation according to claim 1, wherein the phospholipid is selected from the group consisting of dilauroyl-phosphatidyl-choline (DLPC), dimyristoyl-phosphatidylcholine (DMPC), dipalmitoyl-phosphatidyl-choline (DPPC), diarachidoyl-phosphatidylcholine (DAPC), distearoyl-phosphatidyl-choline (DSPC), dioleoyl-phosphatidylcholine (DOPC), 1,2 Distearoyl-sn-glycero-3-ethylphosphocholine (Ethyl-DSPC), dipentadecanoyl-phosphatidylcholine (DPDPC), 1-myristoyl-2-palmitoyl-phosphatidylcholine (MPPC), 1-palmitoyl-2-myristoyl-phosphatidylcholine (PMPC), 1-palmitoyl-2-stearoyl-phosphatidylcholine (PSPC), 1-stearoyl-2-palmitoyl-phosphatidylcholine (SPPC), 1-palmitoyl-2-oleyl-phosphatidyl-choline (POPC), 1-oleyl-2-palmitoyl-phosphatidylcholine (OPPC), dilauroyl-phosphatidylglycerol (DLPG) and its alkali metal salts, diarachidoylphosphatidyl-glycerol (DAPG) and its alkali metal salts, dimyristoylphosphatidylglycerol (DMPG) and its alkali metal salts, dipalmitoylphosphatidylglycerol (DPPG) and its alkali metal salts, distearoylphosphatidyl-glycerol (DSPG) and its alkali metal salts, dioleoyl-phosphatidylglycerol (DOPG) and its alkali metal salts, dilauroyl phosphatidic acid (DLPA), dimyristoyl phosphatidic acid (DMPA) and its alkali metal salts, dipalmitoyl phosphatidic acid (DPPA) and its alkali metal salts, distearoyl phosphatidic acid (DSPA), diarachidoylphosphatidic acid (DAPA) and its alkali metal salts, dilauroyl-phosphatidylethanolamine (DLPE), dimyristoyl-phosphatidylethanolamine (DMPE), dipalmitoylphosphatidylethanolamine (DPPE), distearoyl phosphatidyl-ethanolamine (DSPE), dioleylphosphatidyl-ethanolamine (DOPE), diarachidoyl-phosphatidylethanolamine (DAPE), dilinoleylphosphatidylethanolamine, dilauroyl-phosphatidyl-serine (DLPS), dimyristoyl phosphatidylserine (DMPS), diarachidoyl-phosphatidyl-serine (DAPS), dipalmitoyl phosphatidylserine (DPPS), distearoylphosphatidylserine (DSPS), dioleoyl-phosphatidylserine (DOPS), dipalmitoyl sphingomyelin (DPSP), di stearoyl sphingomyelin (DSSP), dilauroyl-phosphatidylinositol (DLPI), diarachidoylphosphatidylinositol (DAPI), dimyristoylphosphatidylinositol (DMPI), dipalmitoylphosphatidylinositol (DPPI), di stearoylphosphatidylinositol (DSPI), and dioleoyl-phosphatidylinositol (DOPI).

8. The pharmaceutical formulation according to claim 7 further comprising a pegylated phospholipid.

9. The pharmaceutical formulation according to claim 7, wherein said fatty acid is selected the group consisting of capric (n-decanoic), lauric (n-dodecanoic), myristic (n-tetradecanoic), palmitic (n-hexadecanoic), stearic (n-octadecanoic), arachidic (n-eicosanoic), behenic (n-docosanoic), and n-tetracosanoic acid.

10. The pharmaceutical formulation according to claim 1, wherein said amphiphilic component covalently bound to the antigen is the phospholipid.

11. A method of using a pharmaceutical formulation in an immunomodulating treatment, wherein the pharmaceutical formulation comprises an aqueous suspension of gas-filled microvesicles with a stabilizing envelope, wherein said stabilizing envelope comprises (a) an antigen covalently bound to an amphiphilic component forming said stabilizing envelope, (b) a phospholipid, and (c) a fatty acid, and wherein the phospholipid and the fatty acid has a molar ratio of lower than 25/75; the method comprising administering the pharmaceutical formulation.

12. The method according to claim 11, wherein said immunomodulating treatment comprises vaccination.

13. The method according to claim 11, wherein said antigen is a vaccine antigen.

14. The method according to claim 11, wherein said immunomodulating treatment comprises a tolerance-inducing treatment.

15. The method according to claim 11, wherein said immunomodulating treatment comprises an immunostimulating treatment.

16. A precursor of a pharmaceutical formulation comprising an aqueous suspension of gas-filled microvesicles with a stabilizing envelope that comprises (a) an antigen covalently bound to an amphiphilic component forming said stabilizing envelope, (b) a phospholipid, and (c) a fatty acid, wherein the phospholipid and the fatty acid has a molar ratio of lower than 25/75; wherein the precursor is in a form of a freeze-dried preparation reconstitutable in a physiologically acceptable aqueous carrier in a presence of a physiologically acceptable gas.

* * * * *